(12) United States Patent
Kim et al.

(10) Patent No.: US 12,168,844 B2
(45) Date of Patent: Dec. 17, 2024

(54) APPARATUS FOR TREATING CLOTHING

(71) Applicant: LG ELECTRONICS INC., Seoul (KR)

(72) Inventors: Dowan Kim, Seoul (KR); Minhyoung Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 17/545,514

(22) Filed: Dec. 8, 2021

(65) Prior Publication Data
US 2022/0098781 A1  Mar. 31, 2022

Related U.S. Application Data

(63) Continuation of application No. 16/349,729, filed as application No. PCT/KR2017/012933 on Nov. 15, 2017, now Pat. No. 11,229,715.

(30) Foreign Application Priority Data

Nov. 18, 2016  (KR) .................. 10-2016-0153744

(51) Int. Cl.
*D06F 35/00* (2006.01)
*A61L 2/08* (2006.01)
*A61L 2/10* (2006.01)

(52) U.S. Cl.
CPC .............. *D06F 35/00* (2013.01); *A61L 2/088* (2013.01); *A61L 2/10* (2013.01); *A61L 2202/11* (2013.01);
(Continued)

(58) Field of Classification Search
CPC ........ A61L 2/088; A61L 2/10; A61L 2202/11; A61L 2202/122; A61L 2202/123; A61L 2202/26
See application file for complete search history.

(56) References Cited

U.S. PATENT DOCUMENTS 5,780,860 A  7/1998  Gadgil et al.
9,028,615 B2  5/2015  Eglmeier et al.
(Continued)

FOREIGN PATENT DOCUMENTS

CN  102907914  2/2013
CN  104695195  6/2015
(Continued)

OTHER PUBLICATIONS

International Search Report (English Translation) and Written Opinion dated Feb. 8, 2018 issued in PCT Application No. PCT/KR2017/012933.
(Continued)

*Primary Examiner* — David E Smith
(74) *Attorney, Agent, or Firm* — KED & ASSOCIATES, LLP

(57) ABSTRACT

Provided in the present invention is an apparatus for treating clothing comprising: a cabinet in which a clothing accommodation space for accommodating clothing is formed; a housing detachably coupled to an inner wall of the clothing accommodation space and provided with a purifying space communicating with the clothing accommodation space; a photocatalyst containing a photocatalytic material and provided inside the housing; and a light source assembly, provided inside the housing, for irradiating light including UV rays by penetrating through the purifying space.

20 Claims, 4 Drawing Sheets

(52) U.S. Cl.
CPC ... *A61L 2202/122* (2013.01); *A61L 2202/123* (2013.01); *A61L 2202/26* (2013.01)

(56) References Cited

U.S. PATENT DOCUMENTS

| | | | |
|---|---|---|---|
| 10,342,888 | B2 | 7/2019 | Park et al. |
| 2008/0168790 | A1 | 7/2008 | Hurlebaus et al. |
| 2008/0307818 | A1 | 12/2008 | Min et al. |
| 2009/0130047 | A1 | 5/2009 | Weiss et al. |
| 2010/0102253 | A1 | 4/2010 | Chang et al. |
| 2013/0052090 | A1 | 2/2013 | Bohlen |
| 2014/0238086 | A1* | 8/2014 | Choi ............... D06F 58/20 68/20 |
| 2014/0368103 | A1 | 12/2014 | Son et al. |
| 2015/0159315 | A1* | 6/2015 | Lim ............... D06F 71/36 38/3 |
| 2015/0292143 | A1* | 10/2015 | Wang ............... D06F 58/203 8/115.53 |
| 2016/0377281 | A1* | 12/2016 | Xu ............... F21V 15/01 362/249.02 |
| 2017/0143868 | A1 | 5/2017 | Huang et al. |
| 2017/0202988 | A1 | 7/2017 | Clark |
| 2017/0327306 | A1* | 11/2017 | Nam ............... B65D 85/18 |
| 2019/0105422 | A1 | 4/2019 | Jeong et al. |
| 2019/0134251 | A1* | 5/2019 | Jeong ............... F25D 17/06 |

FOREIGN PATENT DOCUMENTS

| | | |
|---|---|---|
| JP | H10-323239 | 12/1998 |
| JP | 2000-254515 | 9/2000 |
| JP | 2001-293072 | 10/2001 |
| JP | 2003-339465 | 12/2003 |
| JP | 2004-275758 | 10/2004 |
| JP | 2013-103136 | 5/2013 |
| JP | 2020-513257 | 5/2020 |
| KR | 20-0363962 | 10/2004 |
| KR | 10-2007-0053051 | 5/2007 |
| KR | 10-0839519 | 6/2008 |
| KR | 10-0899948 | 5/2009 |
| KR | 10-2012-0138862 | 12/2012 |
| KR | 10-2013-0015240 | 2/2013 |
| KR | 10-1366267 | 2/2014 |
| KR | 10-2014-0095845 | 8/2014 |
| KR | 10-2015-0014815 | 2/2015 |
| KR | 10-2015-0019189 | 2/2015 |
| KR | 10-2016-0001539 | 1/2016 |
| WO | WO 2014/116065 | 7/2014 |
| WO | WO-2016086848 A1 * | 6/2016 |

OTHER PUBLICATIONS

United States Office Action dated Apr. 7, 2020 issued in co-pending related U.S. Appl. No. 16/349,729.
United States Office Action dated Jul. 14, 2020 issued in co-pending related U.S. Appl. No. 16/349,729.
Chinese Office Action (with English translation) dated Jul. 27, 2020 issued in CN Application No. 201780070882.0.
Japanese Office Action (with English translation) dated Jul. 28, 2020 issued in JP Application No. 2019-526510.
United States Office Action dated Nov. 5, 2020 issued in co-pending related U.S. Appl. No. 16/349,729.
United States Notice of Allowance dated Sep. 9, 2021 issued in co-pending related U.S. Appl. No. 16/349,729.
European Office Action dated Feb. 8, 2023 issued in Application No. 17872288.0.
Japanese Office Action dated Jul. 5, 2022 issued in Application No. 2021-109951.
Korean Office Action dated Nov. 10, 2023 issued in Appln. No. 10-2016-0153744.

* cited by examiner

APPARATUS FOR TREATING CLOTHING

This application is a Continuation Application of U.S. patent application Ser. No. 16/349,729 filed May 14, 2019, which is a U.S. National Stage Application under 35 U.S.C. § 371 of PCT Application No. PCT/KR2017/012933, filed Nov. 15, 2017, which claims priority under 35 U.S.C. § 119 to Korean Patent Application No. No. 10-2016-0153744, filed Nov. 18, 2016, whose entire disclosures are hereby incorporated by reference.

TECHNICAL FIELD

The present invention relates to an apparatus for treating laundry.

BACKGROUND ART

Generally, a laundry treatment device is a device for progressing various works (e.g., washing, drying, deodorizing, unwrinkling, etc.) related to laundry and conceptually includes a washing device for washing laundry, a drying device for drying wet laundry, a refresher for removing odor pervading laundry or wrinkles of laundry, and the like.

Meanwhile, a laundry treatment device tends to be developed to resolve washing, drying, deodorizing and unwrinkling of laundry using a single device. Yet, as such a laundry treatment device employs a drum for receiving laundry therein and a drive device for rotating the drum, it is insufficient to deodorize or unwrinkle the laundry.

Namely, in a laundry treatment device of the related art, while a drum is being rotated, deodorization or unwrinkling is performed in general. Since laundry put in the drum is not in an unwrinkled state but in a wrinkled state, limitation is put on the unwrinkling or deodorizing.

And, in a laundry treatment device of the related art, although steam is jetted for deodorization or sterilization, it is difficult to sterilize high-end laundry made of fur, leather and the like. In case of keeping the sterilized laundry lastingly, there is a problem of re-contamination.

Moreover, in case of sterilizing high-end laundry made of fur, leather or the like by applying UV rays thereto, there is a problem of damaging the laundry.

DISCLOSURE OF THE INVENTION

Technical Task

One technical task of the present invention is to provide an apparatus for treating laundry, by which laundry having difficulty in being sterilized by jetting steam can be sterilized without directly applying UV rays to the laundry.

Another technical task of the present invention is to provide an apparatus for treating laundry, by which recontamination of laundry can be prevented in case of keeping the sterilized laundry lastingly.

Technical Solutions

In one technical aspect of the present invention, provided herein is an apparatus for treating laundry, the apparatus including a cabinet providing a laundry receiving space for receiving the laundry therein, a housing detachably coupled to an inner wall of the laundry receiving space and including a purifying space defined therein to communicate with the laundry receiving space, a photocatalytic member provided within the housing and including a photocatalytic substance, and a light source assembly provided within the housing and applying light including Ultraviolet (UV) rays through the purifying space to the photocatalytic member.

The housing may include a first housing and a second housing detachably attached to an inside of the first housing by defining the purifying space together with the first housing, and a communicating hole may be formed in the first housing so that the laundry receiving space communicates with the purifying space.

The first housing may be projected from an inner wall of the laundry receiving space and the second housing may be embedded in the inner wall of the laundry receiving space.

The first housing may include a cover plate spaced apart from the inner wall of the laundry receiving space and A first flange extending to the inner wall of the laundry receiving space from an edge of the cover plate, and a plurality of the communicating holes may be formed in the first flange.

A plurality of the communicating holes may be formed along the edge of the cover plate and spaced apart from a center of the first housing by a predetermined angle.

The second housing may include a seat plate spaced apart from the cover plate to define the purifying space and a second flange provided to an edge of the seat plate and configured to be coupled to an inside of the first flange.

The photocatalytic member may be coupled to the cover plate and the light source assembly may be coupled to the seat plate and configured to confront the catalytic member.

The cover plate may include a pressurizing rib formed on one surface of the cover plate by extending toward the seat plate and be configured to pressurize the light source assembly toward the seat plate.

The inner wall of the laundry receiving space may include an embedded portion including one recessed surface configured to place the seat plate in the embedded portion and a power supply hole through which an electric cord transferring power to the light source assembly from an external power source passes may be formed in the embedded portion.

A rear sealing part may be provided to one side of the seat plate contacting with the embedded portion so as to seal off the power supply hole from the laundry receiving space.

The seat plate may include a center perforated hole formed in a manner of perforating the seat plate so that the electric cord is connected to the light source assembly.

A front sealing part may be provided to the other side of the seat plate contacting with the light source assembly so as to seal off the center perforated hole from the laundry receiving space.

The light source assembly may include a Light Emitting Diode (LED) Printed Circuit Board (PCB) and a plurality of LED elements disposed on the LED PCB and configured to apply rays including ultraviolet rays to the photocatalytic member.

A plurality of the LED elements may include a plurality of visible ray LED elements disposed in a manner of being spaced apart from each other by a predetermined interval along an edge of the LED PCB and an ultraviolet LED element disposed on a central portion of the LED PCB.

Advantageous Effects

The present invention has an effect of providing an apparatus for treating laundry, by which laundry having difficulty in being sterilized by jetting steam can be sterilized without directly applying UV rays to the laundry.

The present invention has an effect of providing an apparatus for treating laundry, by which recontamination of laundry can be prevented in case of keeping the sterilized laundry lastingly.

BEST MODE FOR INVENTION

An air purifier 30 according to one embodiment of the present invention and a laundry treatment apparatus including the same will be described in detail with reference to the accompanying drawings.

In the following detailed description of the invention includes details to help the full understanding of the present invention. Yet, it is apparent to those skilled in the art that the present invention can be implemented without these details. Occasionally, to avoid obscuring the concept of the present invention, structures and/or devices known to the public may be skipped. Moreover, to help the understanding of the present invention, the accompanying drawings may be illustrated in a manner of exaggerating sizes of some components instead of using a real scale.

Although the terms 'first, second, etc.' may be used herein to describe various elements, these elements should not be limited by these terms. These terms are generally only used to distinguish one element from another.

Terms used in this disclosure are used to describe a specific embodiment only and are not intended to restrict the scope of the appended claims and their equivalents. A singular representation may include a plural representation unless it represents a definitely different meaning from the context. Terms such as "include", "comprise" and "has" are used herein and should be understood that they are intended to indicate the existence of features, numbers, steps, operations, components, parts or combination thereof, disclosed in the specification, and it is also understood that greater or fewer features, numbers, steps, operations, components, parts or combination thereof may likewise be utilized.

Figure 1:
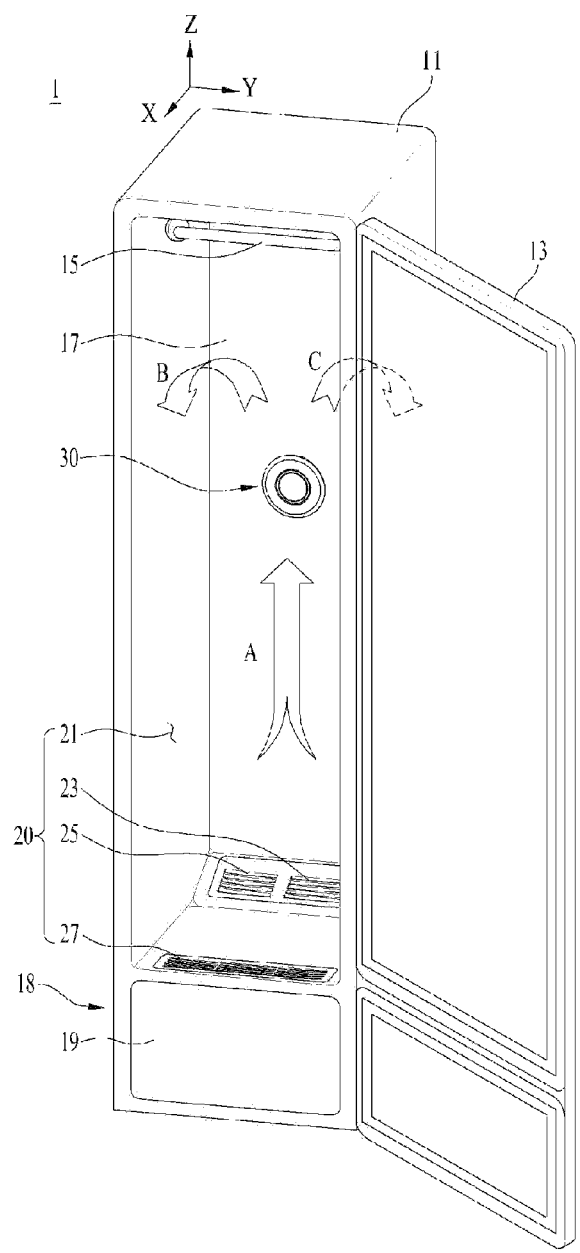
FIG. 1 is a schematic diagram showing a laundry treatment apparatus according to one embodiment of the present invention.

FIG. 1 is a schematic diagram showing a laundry treatment apparatus 1 according to one embodiment of the present invention. Referring to FIG. 1, a laundry treatment apparatus 1 according to one embodiment of the present invention includes a cabinet 11, a laundry receiving part 20 provided within the cabinet 11 so as to provide a laundry receiving space 21 for receiving laundry therein, a door 13 opening/closing the laundry receiving space 21, a supply part supplying at least one of air and moisture to the laundry receiving part 20, and an air purifier 30 provided to the laundry receiving part 20 so as to purify air of the laundry receiving part 20.

The cabinet 11 forms an exterior of the laundry treatment apparatus 1 and a laundry support part 15 is installed in the cabinet 11. The laundry support part 15 includes a bar configured to extend long and may be configured to enable laundry hung thereon to be vibrated in a length direction of the bar. Since the above-functioning laundry support part 15 corresponds to the prior art, its details shall be omitted.

The laundry receiving part 20 provides the laundry receiving space 21 and also includes a moisture discharge portion (or vent) 23 providing moisture to the laundry receiving space 21, an air discharge portion (or vent) 25 providing air to the laundry receiving space 21, and an air suction portion (or vent) 27 sucking the moisture and air of the laundry receiving space 21.

The laundry receiving space 21 is defined by an inner wall. The inner wall includes a rear wall located on a rear side of the cabinet 11, two sidewalls extending from edges of the rear wall toward a front direction, a top wall located over the rear wall and the sidewalls, and a bottom wall located under the rear wall and the sidewalls, and is opened/closed by a door 13. Hereinafter, the inner wall of the laundry receiving space 21 may refer to the rear wall 17 unless mentioned specially.

In the inner wall of the laundry receiving space 21, an embedded portion (or recess) 171, which is formed in a manner that one side is recessed so that a second housing 330 described later can be embedded therein, is formed. The reason why the second housing 330 is embedded is to prevent a step difference generated from the inner wall of the laundry receiving space 21 between a purifying space 31 and the laundry receiving space 21. In the embedded portion 171, a power supply hole 175 is formed so that an electrical cord (not shown) can pass through the power supply hole 175 to deliver power to a light source assembly 352 that will be described later.

In addition, an inner wall recess 173, in which an end point of the housing 310 and 330, i.e., end points of a first and second flanges 313 and 332 are inserted so as to be coupled thereto, is defined in the inner wall of the laundry receiving space 21 in a manner of being recessed toward a rear side of the laundry treatment apparatus 1.

The moisture discharge portion 23 and the air discharge portion 25 discharge moisture and air in a direction of an arrow A, thereby performing deodorizing and unwrinkling functions. In doing so, heated moisture is used mostly.

The air discharge portion 25 sucks the moisture and air circulating along arrows B and C again by being discharged from the moisture discharge portion 23 and the air discharge portion 25. The moisture discharge portion 23, the air discharge portion 25 and a device for operating the air discharge portion 25 are installed in a machine room 18.

The machine room 18 is located in a lower part of the receiving space and may be opened/closed by a machine room door 19.

As the moisture discharge portion 23, the air discharge portion 25 and the device for operating the air discharge portion 25 correspond to the prior art, their details shall be omitted.

The air purifier 30 is installed at the inner wall of the laundry receiving space 21, thereby playing a purifying function of removing contaminants or malodorous substances attached to the laundry in the laundry receiving space 21 using photocatalytic reaction.

Yet, the air purifier 30 does not remove the contaminants or malodorous substances by directly applying UV rays to laundry or directly jetting material generated by UV rays to laundry. If air and moisture of the laundry receiving space 21 and contaminants or malodorous substances detached from laundry enter the purifying space 31 formed in the air purifier 30 together, the air purifier 30 changes the contaminants and the malodorous substances by oxidizing and dissolving the contaminants and the malodorous substances in a manner of generating hydroxyl radicals (·OH) and ozone by applying UV rays to photocatalyst and making them react with the contaminants and malodorous substances.

In this case, the air purifier 30 does not include a separate air suction device for sucking air. Since the air purifier 30 is located on a flow path formed by the moisture and air discharged upward from the moisture discharge portion 23 and the air discharge portion 25 located at the bottom of the laundry receiving part 20, a separate air suction device is not necessary. Therefore, the air purifier 30 can be installed at any place in which a flow path is formed.

The air purifier 30 is described in detail with reference to FIGS. 2 to 4 as follows.

Figure 2:
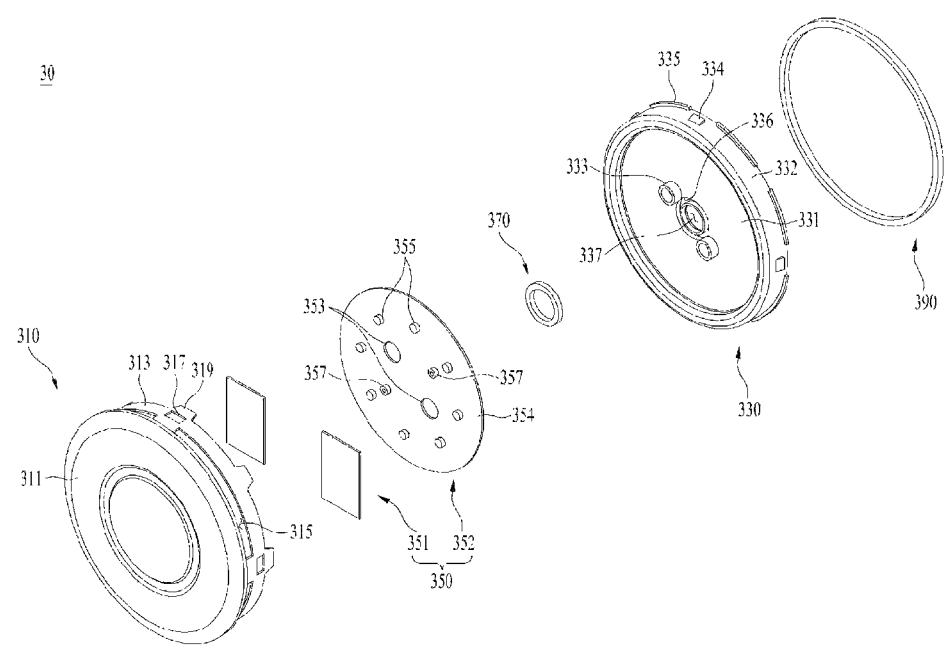
FIG. 2 is an exploded perspective diagram of an air purifier shown in FIG. 1.
Figure 3:
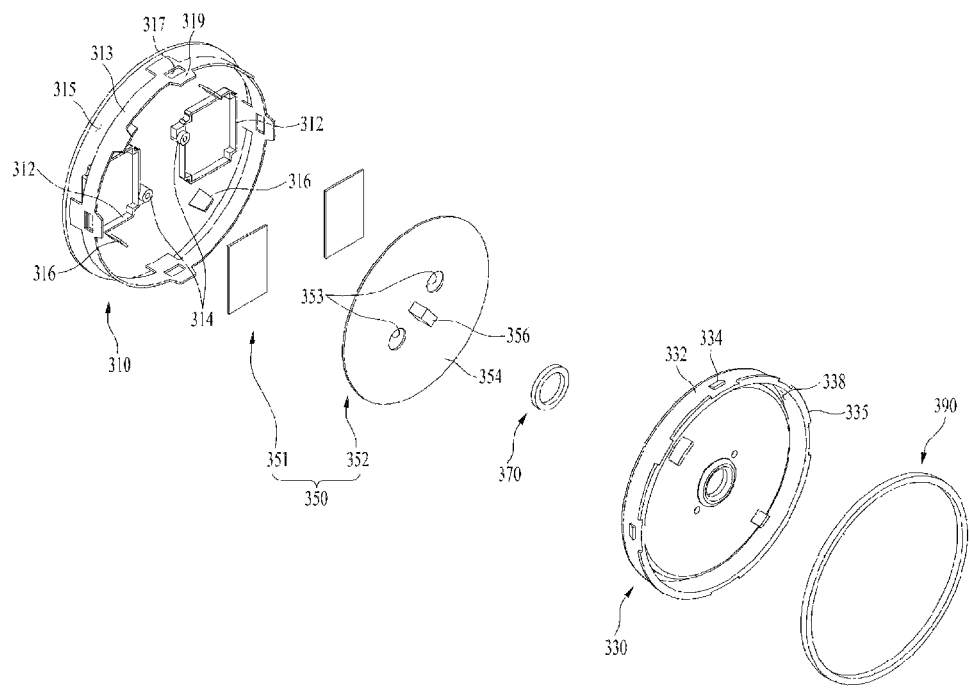
FIG. 3 is an exploded perspective diagram of an air purifier shown in FIG. 1, viewed at a different angle.
Figure 4:
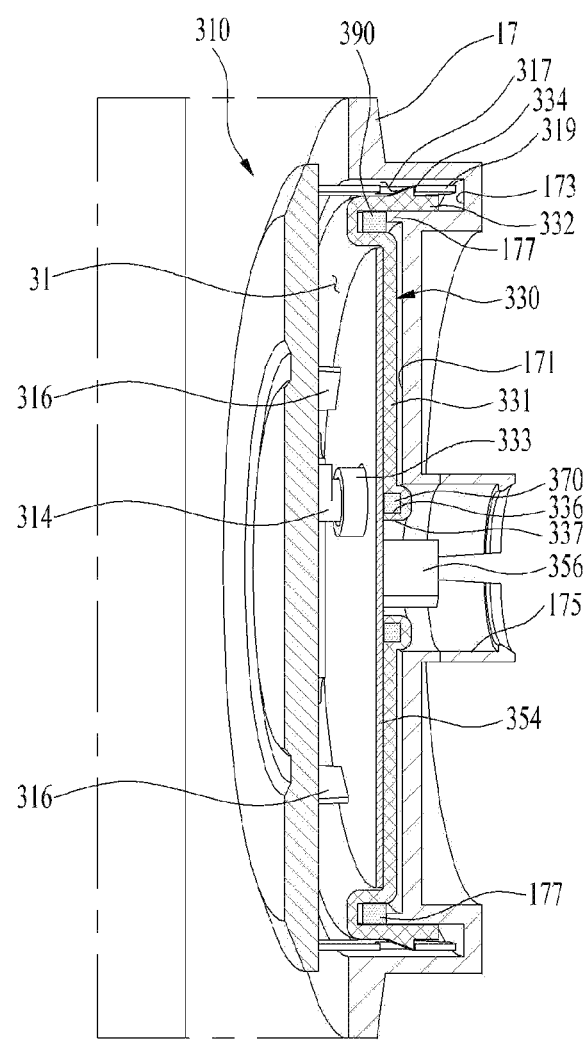
FIG. 4 is a cross-sectional diagram of an air purifier shown in FIG. 1.

FIG. 2 is an exploded perspective diagram of the air purifier 30 shown in FIG. 1, FIG. 3 is an exploded perspective diagram of the air purifier 30 shown in FIG. 1, viewed at a different angle, and FIG. 4 is a cross-sectional diagram of the air purifier 30 shown in FIG. 1.

Referring to FIGS. 2 to 4, the air purifier 30 includes a housing 310 and 330 having a purifying space 31 formed inside, a photocatalytic part 350 provided in the purifying space 31, a sealing part sealing off a power supply hole 175, which is formed in the inner wall of the laundry receiving space 21, from the laundry receiving space 21.

The housing 310 and 330 is detachably coupled to the inner wall of the laundry receiving space 21 and a communicating hole 315 is formed so that the purifying space 31 can communicate with the laundry receiving space 21.

Here, the communicating hole 315 is formed in one side of the housing 310 and 330, i.e., a face approximately vertical to the inner wall of the laundry receiving part 20 so that air and moisture flowing along the inner wall of the laundry receiving part 20 can flow in and be then discharged along the inner wall of the laundry receiving part 20 again.

Particularly, the housing 310 and 330 includes a first housing 310 and a second housing 330 detachably coupled to the first housing 310 and defining the purifying space 31 together with the first housing 310. Here, the second housing 330 is formed to be received within the first housing 310.

The first housing 310 is provided in a manner of being projected from the inner wall 17 of the laundry receiving space 21 so that the air and moisture of the laundry receiving space 21 can be smoothly sucked and discharged. Namely, the first housing 310 includes a cover plate 311 spaced apart from the inner wall 17 of the laundry receiving space 21 and a first flange 313 extending from an edge of the cover plate 311 to the inner wall 17 of the receiving space 21.

The cover plate 311 includes an approximately circular plate and at least an edge portion of the cover plate 311 is formed of a transparent material. This is to enable visible rays emitted from a light emitting diode element 355, which will be described later, to pass through so that a user can check whether the air purifier 30 operates.

The cover plate 311 is provided with a photocatalytic member seat portion 312 formed on a rear side of the cover plate 311 so as to enable a photocatalytic member 351 to be seated thereon, a pressurizing rib 316 pressurizing a light source assembly 352 (described later) in a rear direction, and a spacing member (or spacer) 314 spacing the second housing 330 apart from the first housing 310.

The photocatalytic member seat portion 312 consists of a frame in a rim shape corresponding to a shape of the photocatalytic member 351 so that the photocatalytic member 351 can be received and coupled thereto. As shown in FIG. 3, a couple of the photocatalytic member seat portions 312 may be provided according to the number of the photocatalytic members 351, by which the present invention is non-limited. And, the number of the photocatalytic member seat portions 312 is adjustable if necessary.

The pressurizing rib 316 is formed on a rear side of the cover plate 311, and a plurality of the pressurizing ribs 316 are formed along the edge of the cover plate 311. The pressurizing rib 316 is projected from the rear side of the cover plate 311 so as to pressurize the light source assembly 352, i.e., a Light Emitting Diode Printed Circuit Board (LED PCB) 354 toward the second housing 330 by crossing the purifying space 31.

The spacing member 314 is projected from the rear side of the cover plate 311 and plays a role in spacing the first housing 310 apart from the second housing 330 by pressurizing a support projection 333 (described later) of the second housing 330 toward the second housing 330 so as to define the purifying space 31.

The first flange 313 is formed in an approximately cylindrical shape having both open ends. The first flange 313 includes a communicating hole 315 configured to enable the laundry receiving space 21 and the purifying space 31 to communicate with each other, a hook lock recess 317 into which a hook portion 334 of a second flange 332 (described later) will be locked, and a lock guide 319 facilitating the hook lock recess 317 and the hook portion 334 to be locked together.

A plurality of the communicating holes 315 are formed in a circumferential surface of the first flange 313 along the edge of the cover plate 311. And, the communicating hole 315 is formed by being spaced apart from a center of the first housing 310 by a predetermined angle so that the air and moisture of the laundry receiving space 21 can flow in along the inner wall 17 of the laundry receiving space 21 in all directions. Hence, the communicating hole 315 can perforate the purifying space 31 so that the air and moisture of the laundry receiving space 21 can flow along the inner wall 17 of the laundry receiving space 21 in top, bottom and side directions.

The above-described communicating hole 315 may include a groove extending long along the edge of the cover plate 311 so that the air and moisture of the laundry receiving space 21 can flow in and out more easily. If the first flange 313 is inserted in the inner recess 173, a portion of the communicating hole 315 is disposed on the inner recess 173. Hence, one front side of the seat plate 331 and the inner wall 17 of the laundry receiving space 21 may form a single plane so that the air and moisture of the laundry receiving space 21 can flow in and out of the purifying space 31 easily.

The hook lock recess 317 includes a recess that perforates the first flange 313, and is formed by being spaced apart by a prescribed distance toward the inner wall 17 of the laundry receiving space 21 from a region located between the respective communicating holes 315 so as to maintain the rigidity of the second flange 332.

The lock guide 319 is formed by being projected from an end point of the first flange 313 toward the inner wall 17 of the laundry receiving space 21 so as to be inserted between barrier sills 335 of the second flange 332 (described later). When a user intends to couple the first housing 310 and the second housing 300 together, the hook portion 334 can be locked into the hook lock recess 317 by performing an action of inserting the lock guide 319 between the barrier sills 335, whereby user's convenience can be enhanced.

The second housing 330 is embedded in the inner wall 17 of the laundry receiving space 21 so that the air and moisture of the laundry receiving space 21 can flow in and out smoothly through the communicating hole 315 of the first housing 310. The second housing 330 includes the seat plate 331 spaced apart from the cover plate 311 so as to define the purifying space 31 and a second flange 332 provided to an edge of the seat plate 331 so as to be coupled to an inner side of the first flange 313.

The seat plate 331 is formed in an approximately circular plate shape, and includes a support projection 333 formed on a front side of the seat plate 331 facing the LED PCB 354 so as to support the LED PCB 354, a center perforated hole 337 perforating a central portion of the seat plate 331, a front seat recess portion (or recess) 336 formed to enable a front sealing part (or seal) 370 to be inserted in the front side of the seat plate 331 while enclosing surroundings of the center perforated hole 337, and a rear seat recess portion (or recess) 338 formed to enable a rear sealing part (or seal) 390 to be inserted in a rear side of the seat plate 331 while enclosing surroundings of the center perforated hole 337.

The support projection 333 is projected from the front side of the seat plate 331, and inserted in a projection perforated recess 353 formed in the LED PCB 354 as shown in FIG. 2.

The center perforated hole 337 is formed in a manner of perforating the seat plate 331 so that a pin housing 356 (described later) of the LED PCB can be received in a manner of perforating the center perforated hole 337.

The front seat recess portion 336 is formed to enclose the surroundings of the center perforated hole 337 and configured in a manner of being recessed in a rear direction from the front side of the seat plate 331. As shown in FIG. 2, the front seat recess portion 336 is formed in a shape corresponding to the front sealing part 370.

The rear seat recess portion 338 is formed to enclose the surroundings of the center perforated hole 337 and configured in a manner of being recessed in a front direction from the rear side of the seat plate 331. As shown in FIG. 2, the rear seat recess portion 338 is bigger than the front seat recess portion 336 and formed in a shape corresponding to the rear sealing part 390.

The second flange 332 is formed in an approximately circular shape so that an outer surface of the second flange 332 is coupled to an inner surface of the first flange 331 by being received in the inner side of the first flange 313. The second flange 332 includes a multitude of barrier sills 335 projected from an end point in a diameter direction of the second flange 332 and a hook portion 334 projected from the outer surface of the second flange 332.

Here, a multitude of the barrier sills 335 are provided in a manner of being spaced apart from each other by a predetermined interval but are not provided in rear of a portion to which the hook portion 334 is provided.

The photocatalytic part 350 includes a photocatalytic member 351 containing a photocatalytic substance and a light source assembly 352 configured to apply light to the photocatalytic member 351. The photocatalytic member 351 is seated on a photocatalytic member seat portion 312 formed on the rear side of the cover plate 311 and the light source assembly 352 is seated on the seat plate 331.

Accordingly, the purifying space 31 is defined between the photocatalytic member 351 and the light source assembly 352. The light source assembly 352 applies rays including UV rays to the photocatalytic member 351 across the purifying space 31. The applied UV rays trigger photolytic reaction with the photocatalytic substance of the photocatalytic member 351, thereby generating hydroxyl radicals (·OH) and ozone. Contaminants or malodorous substances having entered the purifying space 31 together with the air and moisture are removed by being dissolved by the hydroxyl radicals (·OH) and ozone.

The photocatalytic member 351 may be formed of such material as non-woven fabric, metal foam or porous metallic material. A photocatalytic substance is coated on at least one surface of the photocatalytic member 351. Two photocatalytic members 351 may be provided as shown in FIG. 2 and FIG. 3, by which the present invention is non-limited. If the photocatalytic member 351 is formed of such material as non-woven fabric, since the photocatalytic member 351 plays a role as a filter that filters off contaminants from the flowing air and moisture, it is more effective to the removal of the contaminants.

The photocatalytic substance may include at least one of a group of $TiO_2$, $ZnO$, $ZrO_2$ and $WO_3$, by which the present invention is non-limited. Furthermore, the photocatalytic substance may employ any substance capable of generating hydroxyl radicals (·OH) and ozone by performing photolytic reaction with UV rays.

The light source assembly 352 includes a Light Emitting Diode (LED) Printed Circuit Board (PCB) and a plurality of LED elements applying rays including UV rays to the photocatalytic member 351 by being disposed on the LED PCB.

The LED PCB 354 is formed in an approximately circular plate shape and has a projection perforated hole 353 formed therein so that the support projection 333 is inserted in the projection perforated hole 353 to be seated and supported on the seat plate 331. Hence, The LED PCB 354 is coupled to the seat plate 331.

Moreover, the LED PCB 354 has a pin (not shown) formed thereon to deliver power to the LED element and is provided with a pin housing 356 for receiving the pin therein.

A plurality of LED elements include a UV LED element 357 applying UV rays and a visible ray LED element 355 applying visible rays.

The UV LED element 357 reacts with the photocatalytic substance to emit UV rays to enable photolysis.

Ultraviolet (UV) rays is a generic term of electromagnetic waves in a wide range including wavelengths of about 397~10 nm, has strong chemical reaction, and is subdivided into near UV rays (wavelength over 290 nm), UV rays of crystal range (crystal transmissive 290~290 nm), Schumann rays (190~120 nm), Lyman rays (120~60 nm), Millikan rays (60 nm or less), etc. UV ray having a wavelength of 190 nm or less is called far UV ray.

As UV ray has a sterilizing effect, and more particularly, a strong sterilizing power. If UV rays having the intensity of 100 μW/cm2 are applied for 1 minute, 99% of colon *Bacillus, Corynebacterium diphtheriae*, dysentery *Bacillus* and the like become extinct.

Therefore, UV rays emitted by the UV LED element 357 may include UV rays in a wavelength range between about 200~400 nm, by which the present invention is non-limited.

The UV LED element 357 is disposed to confront the photocatalytic member 351 so as to apply UV rays to the photocatalytic member 351. As shown in FIG. 2, the UV LED element 357 is disposed on an approximately central portion of the LED PCB 354.

The visible ray LED element 355 plays a role in emitting visible rays to inform a user of presence or non-presence of an operation of the air purifier 30 and may be configured to emit blue visible rays to enable a user to intuitively recognize purification, antibacterialization, or sterilization by seeing the light.

The visible ray LED elements 355 are disposed in a manner of being spaced apart from each other by a predetermined distance along the edge of the LED PCB 354 so as to be recognized by a user. Accordingly, a user can recognize the visible rays through the edge of the cover plate 311 formed of the transparent material. Although the cover plate 311 is formed of material incapable of light transmittance, a user can recognize visible rays according to the light shining effect.

The sealing part 370 and 390 includes the front sealing part 370 and the rear sealing part 390 to cut off air and moisture leaking into the power supply hole 175 through the front and rear sides of the seat plate 331.

The front sealing part 370 plays a role in sealing off the center perforated hole 337, which is connected to the power supply hole 175, from the laundry receiving space 21 so as to prevent air and moisture from permeating into the power supply hole 175 through the center perforated hole 337.

Particularly, the front sealing part 370 is formed in a cylindrical shape so as to enclose the center perforated hole 337 and inserted in the front seat recess portion 336 so as to cut off the air and moisture leaking into the center perforated hole 337 through a gap between the rear side of the LED PCB 354 and the front side of the seat plate 331.

The rear sealing part 390 plays a role in sealing off the power supply hole 175 from the laundry receiving space 21 so as to prevent air and moisture from permeating into the power supply hole 175 through a space between the rear side of the seat plate 331 and the embedded portion 171.

Particularly, like the front sealing part 370, the rear sealing part 390 is formed in a cylindrical shape so as to enclose the center perforated hole 337 and inserted in the rear seat recess portion 338 so as to cut off the air and moisture leaking into the power supply hole 175 through a gap between the rear side of the seat plate 331 and the embedded portion 171.

Meanwhile, an inner wall (17) projection in a shape corresponding to the rear sealing part 390 is formed between the embedded portion 171 and the inner wall recess 173 in a manner of being projected from the embedded portion 171. The inner wall (17) projection pressurizes the rear sealing part 390 provided to the second housing 330, thereby raising an airtight level.

An operation of the air purifier 30 is described in detail with reference to the accompanying drawings as follows.

Referring to FIG. 1, if an operation of the laundry treatment apparatus 1 is initiated, moisture is discharged upward from the moisture discharge portion 23 and air is discharged upward from the air discharge portion 25. Hence, the air and moisture can move upward in Z-axis direction, i.e., along an arrow A.

Meanwhile, the air suction portion 27 located at a spot spaced apart from the moisture discharge portion 23 and the air discharge portion 25 in front direction sucks the discharged air and moisture.

Hence, the air and moisture having moved upward is blocked by the top wall, moves in X- and Y-axis directions, i.e., arrow directions B and C, descends downward, and is then sucked into the air suction portion 27.

Such a flow of the air and moisture can be divided into an ascending flow flowing upward along the rear wall, a front flow flowing in a front direction by being blocked by the top wall, and a descending flow descending along an inner circumference of the door 13. Such flows are approximate and may be formed differently according to the disposition of the laundry in the laundry receiving space 21.

In this case, regarding the laundry hung on the laundry support part 15, as the laundry support part 15 vibrates in a length direction of the bar, contaminants and malodorous substances attached to the laundry are detached from the laundry.

The contaminants and malodorous substances attached to the laundry are detached from the laundry and then move in the laundry receiving space 21 according to the flows of the air and moisture.

In doing so, since the air purifier 30 is provided in a manner of being projected from the inner wall 17 of the laundry receiving space 21, i.e., the rear wall, the contaminants and malodorous substances moving upward along the flow of the air and moisture enter the purifying space 31 of the air purifier 30 through the communicating hole 315.

In this case, since the communicating holes 315 are formed in side portions of the housing 310 and 330 as well as in the top and bottom of the housing 310 and 330, the contaminants and malodorous substances can enter the purifying space 31 along the changed flow of the air and moisture.

The contaminants and malodorous substances having entered the purifying space 31 are removed in a manner of being oxidized and dissolved into non-hazardous water and carbon dioxide gas by the hydroxyl radicals (·OH) and ozone generated from the photolytic reaction with UV rays. The contaminants include germs. Since such germs are organic compounds, cell walls of the germs are damaged by strong oxidization of the photocatalyst, whereby sterilization is performed by oxidization and decomposition of the germs.

As described above, while the present invention has been described and illustrated herein with reference to the preferred embodiments thereof, this description is intended to be illustrative, and not to limit the scope of the claims. Thus, it is intended that the present invention covers the modifications and variations of this invention provided they come within the scope of the appended claims and their equivalents.

What is claimed is:

1. An apparatus for treating laundry, the apparatus comprising:
   a cabinet;
   a laundry receiving space located in the cabinet for receiving laundry therein, the laundry receiving space comprising a rear wall located on a rear side of the cabinet, two sidewalls extending from edges of the rear wall toward a front direction, a top wall located over the rear wall and the sidewalls, a bottom wall located under the rear wall and the sidewalls, and an opening;
   a door configured to open or close the opening;
   a laundry support part installed in the cabinet and including a hanger bar extended along a width-direction of the cabinet;
   an air suction portion located in a front side of a lower portion of the laundry receiving space, and configured to suck air in the laundry receiving space;
   an air discharge portion located in the rear side of the lower portion of the laundry receiving space, and configured to discharge air in the laundry receiving space; and
   an air treating part located at the rear wall of the laundry receiving space and comprising a UV emitting source configured to emit ultraviolet (UV) rays,
   wherein at least a part of the air that is sucked through the air suction portion flows through the air treating part, and wherein the air treating part comprises:
  a housing defining a purified space; and
  an opening located at the housing to allow the purified space to communicate with the laundry receiving space.

2. The apparatus of claim 1, wherein the opening is provided in a plurality.

3. The apparatus of claim 1, wherein the air treating part comprises:
  a sealing part to seal off the air and moisture of the laundry receiving space.

4. The apparatus of claim 1, wherein the UV emitting source is provided within the housing and configured to emit ultraviolet (UV) rays toward the purified space.

5. The apparatus of claim 4, wherein the UV emitting source comprises:
  a light emitting diode (LED) printed circuit board (PCB); and
  a plurality of LED elements disposed on the LED PCB and configured to emit ultraviolet (UV) rays.

6. The apparatus of claim 5, wherein the plurality of LED elements spaced apart from each other.

7. The apparatus of claim 1, wherein the housing comprises:
  a first housing; and
  a second housing coupled to the first housing to define at least a part of the purified space with the first housing and located between the first housing and the rear wall of the laundry receiving space.

8. The apparatus of claim 7, wherein the UV emitting source is provided inside the housing and configured to emit ultraviolet (UV) rays to the purified space, and
wherein the UV emitting source emits the UV rays in either one direction from the second housing toward the first housing or from the first housing toward the second housing.

9. The apparatus of claim 8, wherein the housing further comprises:
  a housing penetration hole through which an electric wire passes to be connected to the UV emitting source.

10. The apparatus of claim 1, wherein at least the part of the air moves along an airflow generated by the air discharge portion after flowing through the air treating part.

11. The apparatus of claim 1, wherein the air discharged from the air discharge portion moves upward along an inner wall of the laundry receiving space.

12. The apparatus of claim 11, wherein the upwardly discharged air moves downward by a top wall of the laundry receiving space.

13. The apparatus of claim 1, wherein contaminants and malodorous substances attached to the laundry are detached from the laundry and move along the airflow generated by the air discharge portion, based on a vibration of the hanger bar.

14. The apparatus of claim 1, wherein the air treating part is disposed on the rear wall with a corresponding height between a height of hanger bar and a height of the air discharge portion.

15. An apparatus for treating laundry, the apparatus comprising:
  a cabinet;
  a laundry receiving space located in the cabinet for receiving laundry therein, the laundry receiving space comprising a rear wall located on a rear side of the cabinet, two sidewalls extending from edges of the rear wall toward a front direction, a top wall located over the rear wall and the sidewalls, a bottom wall located under the rear wall and the sidewalls, and an opening;
  a door configured to open or close the opening;
  an air suction portion configured to suck air in the laundry receiving space;
  an air discharge portion configured to discharge air in the laundry receiving space; and
  an air treating part located at the rear wall of the laundry receiving space,
  wherein at least a part of the air that is sucked through the air suction portion flows through the air treating part,
  wherein the air treating part is provided between the bottom wall and the top wall, and
  wherein the air treating part comprises:
    a housing defining a space; and
    an opening located at the housing to allow the space to communicate with the laundry receiving space.

16. The apparatus of claim 15, wherein the housing defines a purified space.

17. The apparatus of claim 15, wherein the air treating part is spaced from the bottom wall and the top wall.

18. The apparatus of claim 15, wherein the air suction portion is located in a front side of a lower portion of the laundry receiving space, and
wherein the air discharge portion is located in the rear side of the lower portion of the laundry receiving space.

19. The apparatus of claim 15, wherein the air treating part comprises a UV emitting source configured to emit ultraviolet (UV) rays.

20. The apparatus of claim 15, further comprising a laundry support part installed in the cabinet and including a hanger bar extended along a width-direction of the cabinet.

* * * * *